(12) United States Patent
Liu et al.

(10) Patent No.: US 11,293,027 B2
(45) Date of Patent: Apr. 5, 2022

(54) **RECOMBINANT *BACILLUS SUBTILIS* WITH IMPROVED 2'-FUCOSYLLACTOSE PRODUCTION, AND CONSTRUCTION METHOD THEREOF**

(71) Applicant: JIANGNAN UNIVERSITY, Wuxi (CN)

(72) Inventors: Long Liu, Wuxi (CN); Jian Chen, Wuxi (CN); Xueqin Lv, Wuxi (CN); Guocheng Du, Wuxi (CN); Jianghua Li, Wuxi (CN); Jieying Deng, Wuxi (CN); Ke Liu, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 17/132,768

(22) Filed: Dec. 23, 2020

(65) Prior Publication Data
US 2021/0363535 A1 Nov. 25, 2021

(30) Foreign Application Priority Data

May 25, 2020 (CN) .......................... 202010449420.3

(51) Int. Cl.
| | | |
|---|---|---|
| *C12N 15/62* | (2006.01) | |
| *C12N 9/10* | (2006.01) | |
| *C12N 9/12* | (2006.01) | |
| *C12N 15/75* | (2006.01) | |
| *C12P 19/18* | (2006.01) | |

(52) U.S. Cl.
CPC ........... *C12N 15/62* (2013.01); *C12N 9/1051* (2013.01); *C12N 9/1205* (2013.01); *C12N 15/75* (2013.01); *C12P 19/18* (2013.01)

(58) Field of Classification Search
CPC ...... C12N 15/62; C12N 9/1051; C12N 15/75; C12N 9/1205; C12P 19/18
See application file for complete search history.

(56) References Cited

U.S. PATENT DOCUMENTS 7,943,733 B2 * 5/2011 Shen .................... C07K 14/001 530/350
9,278,138 B2 * 3/2016 Cheng ...................... A61K 8/64

OTHER PUBLICATIONS

Arai et al., Design of the linkers which effectively separate domains of a bifunctional fusion protein. Prot. Eng., 2001, vol. 14(8): 529-532. (Year: 2001).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Deng et al., Engineering the Substrate Transport and Cofactor Regeneration Systems for Enhancing 2'-Fucosyllactose Synthesis in Bacillus subtilis. ACS Synth. Biol., 2019, vol. 8: 2418-2427. (Year: 2019).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Yu et al., Synthetic fusion protein design and applications. Biotechnol. Advances., 2015, vol. 33: 155-164. (Year: 2015).*

* cited by examiner

*Primary Examiner* — Ganapathirama Raghu
(74) *Attorney, Agent, or Firm* — SZDC Law P.C.

(57) ABSTRACT

The present invention provides a recombinant *Bacillus subtilis* with improved 2'-fucosyllactose production, and a construction method thereof. In the present invention, a strain capable of efficiently synthesizing 2'-fucosyllactose is obtained by the fusion expression of the fucosyltransferase gene and the L-fucokinase/guanosine 5'-diphosphate-L-fucose pyrophosphorylase gene in *Bacillus subtilis* BSGL-FF, the fermentation supernatant of which comprises a cumulative amount of 2'-fucosyllactose as high as 1.62 g/L, which is 55% higher than the amount achieved with the control strain. The construction method of the recombinant *Bacillus subtilis* of the present invention is simple, and convenient to use, and thus has good application prospects.

6 Claims, 5 Drawing Sheets

Specification includes a Sequence Listing.

RECOMBINANT *BACILLUS SUBTILIS* WITH IMPROVED 2'-FUCOSYLLACTOSE PRODUCTION, AND CONSTRUCTION METHOD THEREOF

This application is claims priority to Chinese Patent Application No. 202010449420.3, filed on May 25, 2020, which is incorporated by reference for all purposes as if fully set forth herein.

FIELD OF THE INVENTION

The present invention relates to the technical field of metabolic engineering, and more particularly to a recombinant *Bacillus subtilis* with improved 2'-fucosyllactose production, and a construction method thereof.

DESCRIPTION OF THE RELATED ART

Human milk contains important nutrients, biologically active substances, and factors that stimulate the growth of intestinal flora. Among them, human milk oligosaccharides (HMOs) play a key role in many physiological functions, such as promoting the growth of bifidobacteria, inhibiting pathogen infection, and improving immune response. The fucosylated oligosaccharides (FOSs) from human milk oligosaccharides have attracted great attention due to their physiological functions such as ability to act as receptor analogues of intestinal pathogenic bacteria, ability to promote immune regulation and ability to reduce inflammation.

In the past few years, 2'-FL was initially produced through microbial fermentation. In 2012, 2'-FL was first produced by transformed *E. coli* through fed-batch fermentation of high cell density cultivation and whole cell biosynthesis, and the 2'-FL synthesized by microorganisms was identified by LC/MS. Also, metabolic engineering strategies were performed on *E. coli*, including deleting the Lac operon, deleting the wcaJ and lon genes (where the Lon protease degrades positive regulator RcsA and others) downstream of the GDP-L-fucose gene. First, FucT2 from *Helicobacter pylori* 26695 was selected for FucT2 biosynthesis. Then the four de novo biosynthesis genes manB, manC, gmd and wcaG were overexpressed, and a replenishment pathway was also introduced into engineered *E. coli*. In order to further increase the production of 2'-FL from the de novo and replenishment pathways, the genes fucI and fucK were knocked out, and 11 FucT2 candidate genes were screened.

*Bacillus subtilis* is a widely used host for producing enzyme preparations for use in food and important nutritional chemicals. Its products have been certified by the FDA as the "generally regarded as safe" (GRAS) safety level. However, the expression levels of heterologous fucosyltransferase, and L-fucokinase/guanosine 5'-diphosphate-L-fucose pyrophosphorylase in existing *Bacillus subtilis* producing 2'-FL are low, which limits the synthesis of 2'-FL in recombinant *Bacillus subtilis*.

SUMMARY OF THE INVENTION

In order to solve the above technical problems, in the present invention, the intracellular expressions of fucosyltransferase and L-fucokinase/guanosine 5'-diphosphate-L-fucose pyrophosphorylase are effectively increased by expressing a fusion protein of FKP (L-fucokinase/guanosine 5'-diphosphate-L-fucose pyrophosphorylase) with FutC (fucosyltransferase), to promote the synthesis of 2'-fucosyllactose.

A first object of the present invention is to provide a recombinant *Bacillus subtilis* with improved 2'-fucosyllactose production. The recombinant *Bacillus subtilis* is obtained by over-expressing a fusion protein of L-fucokinase/guanosine 5'-diphosphate-L-fucose pyrophosphorylase (FKP) and fucosyltransferase (FutC) in *Bacillus subtilis* BSGL. The *Bacillus subtilis* BSGL is obtained by enhancing the expression of the lactose transporter gene in the genome of *Bacillus subtilis* 168.

Preferably, the L-fucokinase/guanosine 5'-diphosphate-L-fucose pyrophosphorylase (FKP) is conjugated to the fucosyltransferase (FutC) by a linker.

Preferably, the amino acid sequence of the linker is as shown in SEQ ID NO:4, SEQ ID NO:5 or SEQ ID NO:6.

The construction method of *Bacillus subtilis* BSGL of the present invention is as described in Example 1 of Patent No. 201910093684.7, in which the amyE site of the amylase gene in *Bacillus subtilis* 168 is replaced by the P43 promoter and lactose transporter gene to enhance the expression of the lactose transporter gene in *Bacillus subtilis* 168. The lactose transporter gene is as shown by Gene ID: 949083 in NCBI.

The L-fucokinase/guanosine 5'-diphosphate-L-fucose pyrophosphorylase gene of the present invention is derived from *Bacteroides fragilis*, and the fucosyltransferase is derived from *Helicobacter pylori*.

Preferably, the nucleotide sequence of the L-fucokinase/guanosine 5'-diphosphate-L-fucose pyrophosphorylase gene is as shown by GenBank: AY849806.1 on NCBI.

Preferably, the nucleotide sequence of the fucosyltransferase is as shown by GenBank: KY499613 on NCBI.

Preferably, the recombinant *Bacillus subtilis* comprises pP43-mpd as an expression vector.

A second object of the present invention is to provide a method for constructing the recombinant *Bacillus subtilis*, which comprises the following steps:

S1: constructing a recombinant plasmid containing the L-fucokinase/guanosine 5'-diphosphate-L-fucose pyrophosphorylase gene, the fucosyltransferase gene and a linker gene; and S2: transforming the recombinant plasmid into the competent *Bacillus subtilis* BSGL cells, and confirming, by verification, the successful expression of a fusion protein of the L-fucokinase/guanosine 5'-diphosphate-L-fucose pyrophosphorylase and the fucosyltransferase, to obtain the recombinant *Bacillus subtilis*.

A third object of the present invention is to provide a method for producing 2'-fucosyllactose by fermentation with the recombinant *Bacillus subtilis*.

Preferably, the method comprises the following steps:

S1: inoculating single colonies of recombinant *E. coli* in a seed culture medium and culturing for 8-12 h to prepare a seed culture; and S2: inoculating the seed culture into a fermentation medium, incubating at 34-36° C. and 180-220 rpm for 20-30 h, and separating the fermentation supernatant to obtain 2'-fucosyllactose.

Preferably, the seed culture medium comprises 8-12 g/L of tryptone, 4-6 g/L of yeast powder, and 8-12 g/L of NaCl.

Preferably, the fermentation medium comprises 15-25 g/L of initial glycerol, 5-7 g/L of peptone, 10-15 g/L of powdery yeast, 5-7 g/L of $(NH_4)_2SO_4$, 12-13 g/L of $K_2HPO_4 \cdot 3H_2O$, 2-3 g/L of $KH_2PO_4$, 4-6 g/L of $CaCO_3$ and 8-12 mL/L of a trace element solution. The trace elements solution includes 0.8-1.2 g/L of $MnSO_4 \cdot 5H_2O$, 0.3-0.5 g/L of $CoCl_2 \cdot 6H_2O$, 0.1-0.3 g/L of $NaMoO_4 \cdot 2H_2O$, 0.1-0.3 g/L of $ZnSO_4 \cdot 7H_2O$, 0.08-0.12 g/L of $AlCl_3 \cdot 6H_2O$, 0.08-0.12 g/L of $CuCl_2 \cdot H_2O$, 0.04-0.06 g/L of $H_3BO_4$, and 4-6M HCl.

The present invention has the following beneficial effects.

In the present invention, a strain capable of efficiently synthesizing 2'-fucosyllactose is obtained by the fusion expression of the fucosyltransferase gene and the L-fucokinase/guanosine 5'-diphosphate-L-fucose pyrophosphorylase gene in *Bacillus subtilis* BSGL-FF, the fermentation supernatant of which comprises a cumulative amount of as high as 1.62 g/L, which is 55% higher than the amount achieved with the control strain. The construction method of the recombinant *Bacillus subtilis* of the present invention is simple, and convenient to use, and thus has good application prospects.

DETAILED DESCRIPTION OF THE PREFERRED EMBODIMENTS

The present invention will be further described below with reference to the accompanying drawings and specific examples, so that those skilled in the art can better understand and implement the present invention; however, the present invention is not limited thereto.

Example 1: Expression of Fusion Protein FR, FR-EK1, FR-EK2, and FR-EK3

According to the sequence of L-fucokinase/guanosine 5'-diphosphate-L-fucose pyrophosphorylase gene fkp of *Bacteroides fragilis* (ATCC No. 25285) and the sequence of futC gene of *Helicobacter pylori* (ATCC No. 26695) published on NCBI, the recombinant plasmids pP43-FR (without a linker), pP43-FR-EK1 (EK1 linker), pP43-FR-EK2 (EK2 linker), and pP43-FR-EK3 (EK3 linker) were constructed by the PCR amplification and one-step cloning ligation of the genes ftp and futC and the plasmid pP43-mpd, where the nucleotide sequence of EK1 linker is as shown in SEQ ID NO:1, the nucleotide sequence of EK2 linker is as shown in SEQ ID NO:2, the nucleotide sequence of EK3 linker is as shown in SEQ ID NO:3, and the plasmid maps are shown in FIGS. 1, 2, 3 and 4.

The constructed recombinant plasmid was transformed in an amount of 50-300 ng into competent cells of recombinant *Bacillus subtilis* BSGL (see *Bacillus subtilis* 168L constructed in Example 1 of Patent No. 201910093684.7) by electroporation at a voltage of 2.5 kV for 5 ms. After recovery at 37° C. for 5 h, the cells were inoculated into an LB plate coated with kanamycin having a final concentration of 10 μg/mL, and aerobically incubated at 37° C. for 12 h. Several single colonies were picked up.

After screening of resistance strains on the kanamycin plate, verification of kanamycin resistance by colony PCR and sequencing, it was confirmed that whether a fusion protein of fucosyltransferase with L-fucokinase/guanosine 5'-diphosphate-L-fucose pyrophosphorylase was successfully expressed. The *Bacillus subtilis* that was kanamycin resistance positive, verified by colony PCR with a certain band, had a sequencing result consistent with the theoretical result was the successfully transformed *Bacillus subtilis*, in which the fusion protein of fucosyltransferase with L-fucokinase/guanosine 5'-diphosphate-L-fucose pyrophosphorylase was successfully expressed.

It was confirmed that the L-fucokinase/guanosine 5'-diphosphate-L-fucose pyrophosphorylase from *Bacteroides fragilis* and fucosyltransferase were successfully expressed, and the recombinant *Bacillus subtilis* BSGL-FR, BSGL-FR-EK1, BSGL-FR-EK2, and BSGL-FR-EK3 were obtained.

Example 2: Production of 2'-Fucosyllactose by Fermentation with BSGL-FR-EK1

The recombinant *Bacillus subtilis* BSGL-FR-EK1 was prepared into a seed culture. The seed culture medium for the seed culture contained 10 g/L of peptone, 5 g/L of yeast powder, and 10 g/L of NaCl. The seed culture was prepared by picking single colonies on fresh plates into the seed culture mediums and cultured for 8-10 h.

The seed culture was inoculated into a fermentation medium in an amount to give an $OD_{600}$ value of 0.1. The fermentation medium contained 20 g/L of initial glycerol, 6 g/L of peptone, 12 g/L of yeast powder, 6 g/L of $(NH_4)_2SO_4$, 12.5 g/L of $K_2HPO_4.3H_2O$, 2.5 g/L of $KH_2PO_4$, 5 g/L of $CaCO_3$, and 10 mL/L of a trace element solution comprising 1.0 g/L of $MnSO_4.5H_2O$, 0.4 g/L of $CoCl_2.6H_2O$, 0.2 g/L of $NaMoO_4.2H_2O$, 0.2 g/L of $ZnSO_4.7H_2O$, 0.1 g/L of $AlCl_3.6H_2O$, 0.1 g/L of $CuCl_2.H_2O$, 0.05 g/L of $H_3BO_4$, and 5M HCl. Then the cells were incubated at 35° C. and 200 rpm for 24 h.

Figure 1:
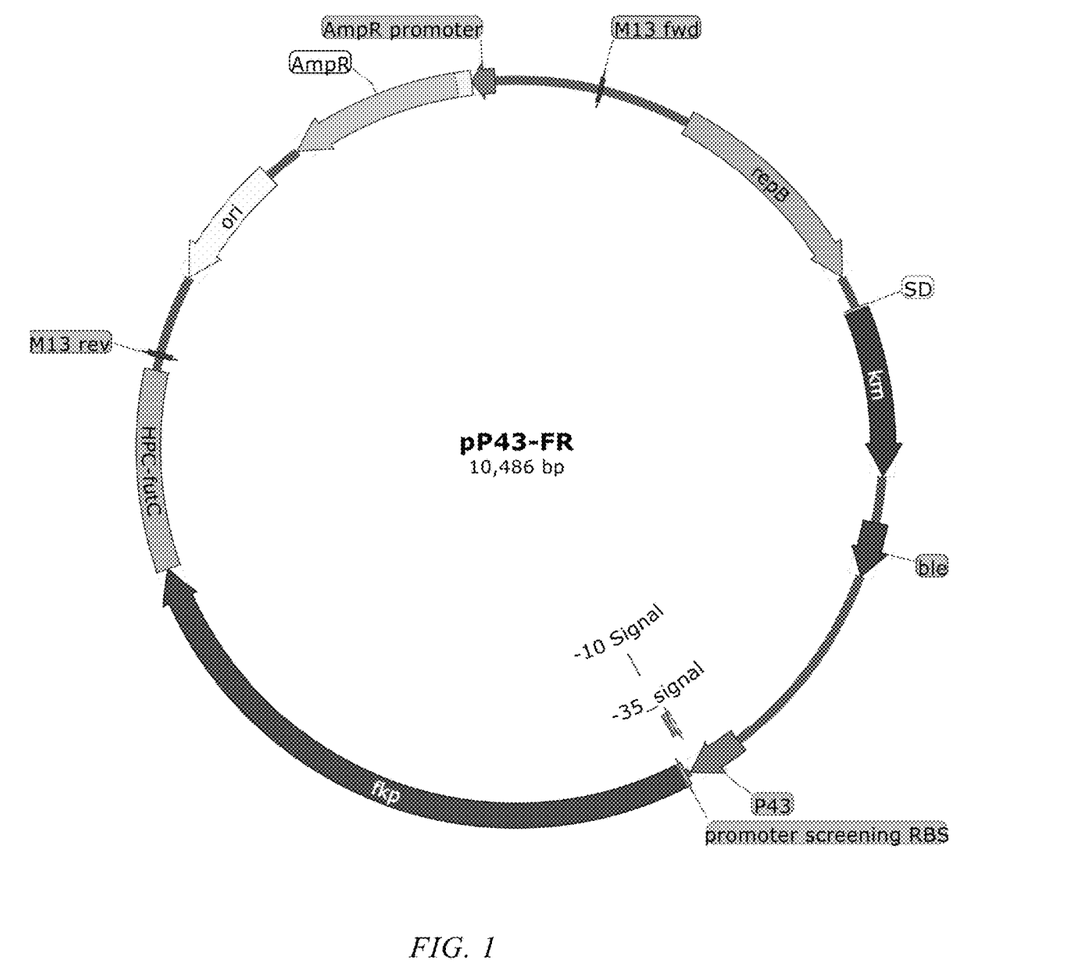
FIG. 1 is a map of pP43-FR plasmid.
Figure 2:
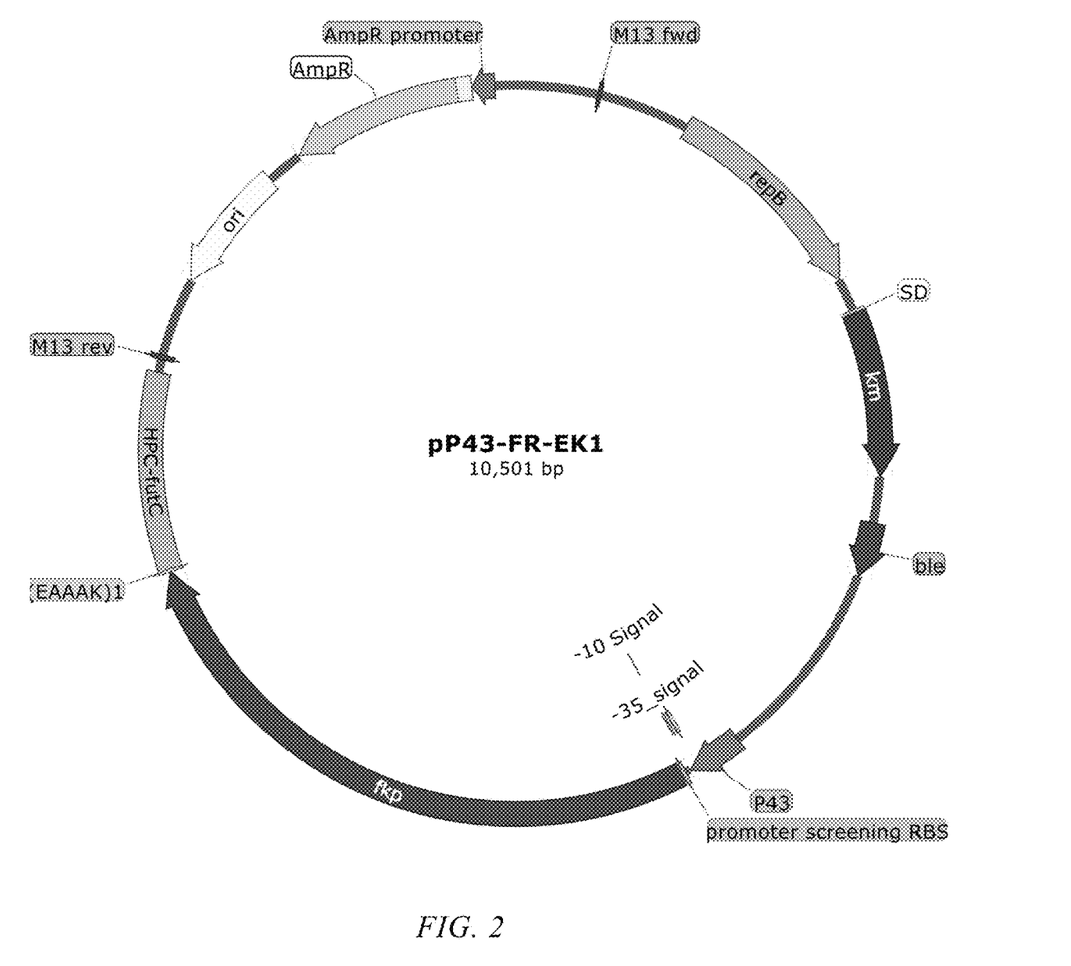
FIG. 2 is a map of pP43-FR-EK1 plasmid.
Figure 3:
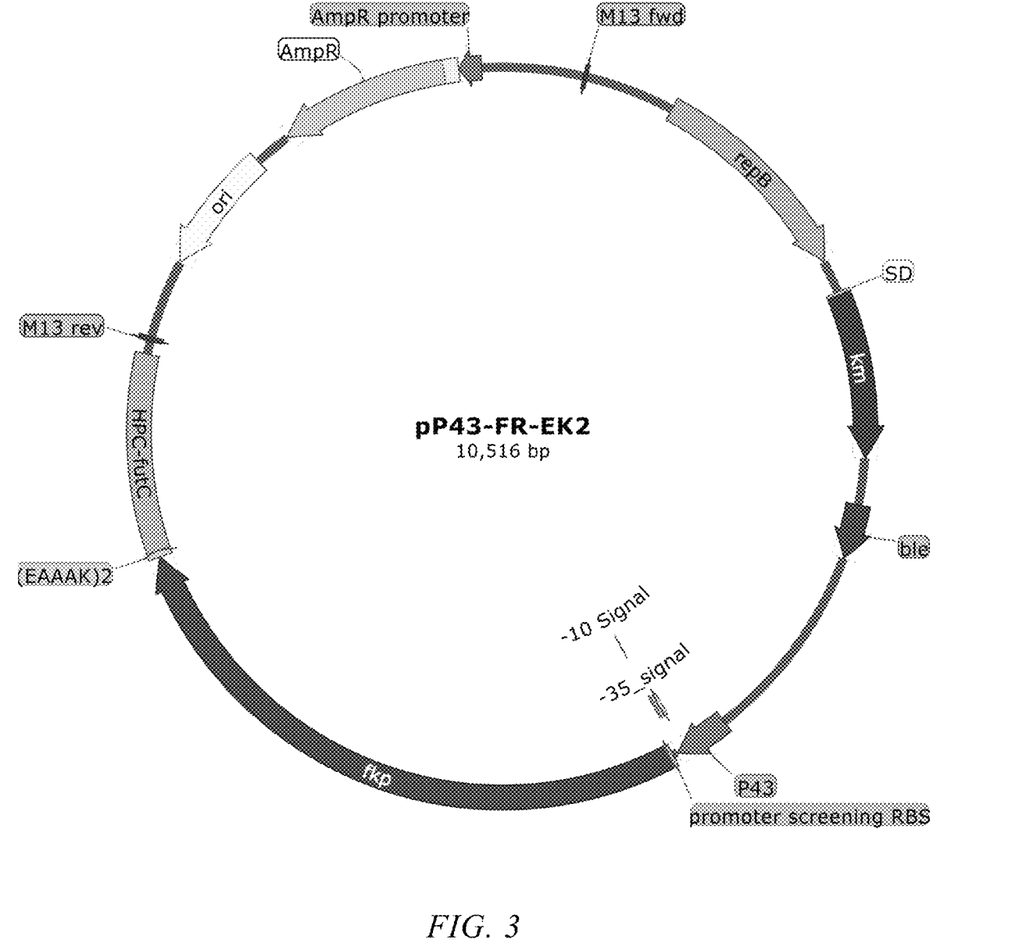
FIG. 3 is a map of pP43-FR-EK2 plasmid.
Figure 4:
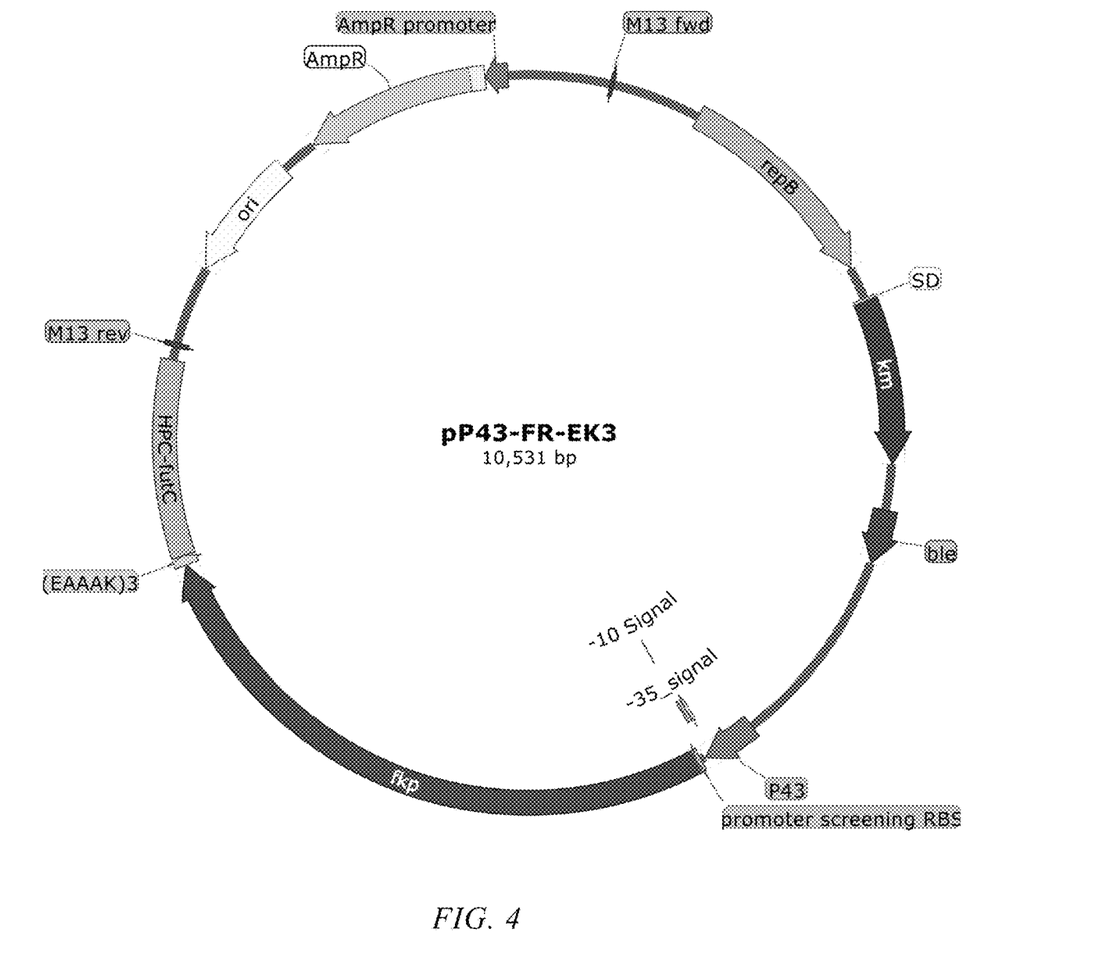
FIG. 4 is a map of pP43-FR-EK3 plasmid.
Figure 5:
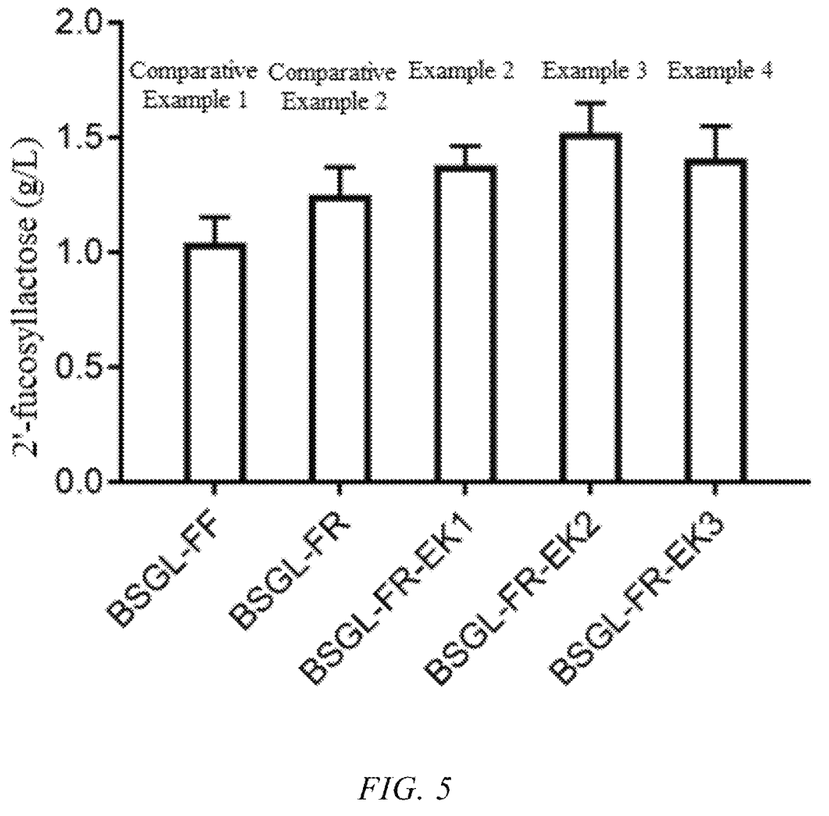
FIG. 5 shows the content of 2'-fucosyllactose in examples.

After the fermentation, the content of 2'-fucosyllactose in the fermentation supernatant was determined by high performance liquid chromatography. The content of 2'-fucosyllactose is determined to be up to 1.380 g/L (FIG. 5).

Example 3: Production of 2'-Fucosyllactose by Fermentation with BSGL-FR-EK2

The recombinant *Bacillus subtilis* BSGL-FR-EK2 was prepared into a seed culture. The seed culture medium for the seed culture contained 10 g/L of peptone, 5 g/L of yeast powder, and 10 g/L of NaCl. The seed culture was prepared by picking single colonies on a fresh plate into the seed culture medium and cultured for 8-10 h.

The seed culture was inoculated into a fermentation medium in an amount to give an $OD_{600}$ value of 0.1. The fermentation medium contained 20 g/L of initial glycerol, 6 g/L of peptone, 12 g/L of yeast powder, 6 g/L of $(NH_4)_2SO_4$, 12.5 g/L of $K_2HPO_4.3H_2O$, 2.5 g/L of $KH_2PO_4$, 5 g/L of $CaCO_3$, and 10 mL/L of a trace element solution comprising 1.0 g/L of $MnSO_4.5H_2O$, 0.4 g/L of $CoCl_2.6H_2O$, 0.2 g/L of $NaMoO_4.2H_2O$, 0.2 g/L of $ZnSO_4.7H_2O$, 0.1 g/L of $AlCl_3.6H_2O$, 0.1 g/L of $CuCl_2.H_2O$, 0.05 g/L of $H_3BO_4$, and 5M HCl. Then the cells were incubated at 35° C. and 200 rpm for 24 h.

After the fermentation, the content of 2'-fucosyllactose in the fermentation supernatant was determined by high performance liquid chromatography. The content of 2'-fucosyllactose is determined to be up to 1.620 g/L (FIG. 5).

Example 4: Production of 2'-Fucosyllactose by Fermentation with BSGL-FR-EK3

The recombinant *Bacillus subtilis* BSGL-FR-EK3 was prepared into a seed culture. The seed culture medium for the seed culture contained 10 g/L of peptone, 5 g/L of yeast powder, and 10 g/L of NaCl. The seed culture was prepared by picking single colonies on a fresh plate into the seed culture medium and cultured for 8-10 h.

The seed culture was inoculated into a fermentation medium in an amount to give an $OD_{600}$ value of 0.1. The fermentation medium contained 20 g/L of initial glycerol, 6 g/L of peptone, 12 g/L of yeast powder, 6 g/L of $(NH_4)_2SO_4$, 12.5 g/L of $K_2HPO_4.3H_2O$, 2.5 g/L of $KH_2PO_4$, 5 g/L of $CaCO_3$, and 10 mL/L of a trace element solution comprising 1.0 g/L of $MnSO_4.5H_2O$, 0.4 g/L of $CoCl_2.6H_2O$, 0.2 g/L of $NaMoO_4.2H_2O$, 0.2 g/L of $ZnSO_4.7H_2O$, 0.1 g/L of $AlCl_3.6H_2O$, 0.1 g/L of $CuCl_2.H_2O$, 0.05 g/L of $H_3BO_4$, and 5 M HCl. Then the cells were incubated at 35° C. and 200 rpm for 24 h.

After the fermentation, the content of 2'-fucosyllactose in the fermentation supernatant was determined by high performance liquid chromatography. The content of 2'-fucosyllactose is determined to be up to 1.410 g/L (FIG. 5).

Comparative Example 1: Production of 2'-Fucosyllactose by Fermentation with BSGL-FF The recombinant *Bacillus subtilis* BSGL-FF (see *Bacillus subtilis* 168L-FF constructed in Example 2 of Patent No. 201910093684.7) was prepared into a seed culture. The seed culture medium for the seed culture contained 10 g/L of peptone, 5 g/L of yeast powder, and 10 g/L of NaCl. The seed culture was prepared by picking single colonies on a fresh plate into the seed culture medium and cultured for 8-10 h.

The seed culture was inoculated into a fermentation medium in an amount to give an $OD_{600}$ value of 0.1. The fermentation medium contained 20 g/L of initial glycerol, 6 g/L of peptone, 12 g/L of yeast powder, 6 g/L $(NH_4)_2SO_4$, 12.5 g/L of $K_2HPO_4.3H_2O$, 2.5 g/L of $KH_2PO_4$, 5 g/L of $CaCO_3$, and 10 mL/L of a trace element solution comprising 1.0 g/L of $MnSO_4.5H_2O$, 0.4 g/L of $CoCl_2.6H_2O$, 0.2 g/L of $NaMoO_4.2H_2O$, 0.2 g/L of $ZnSO_4.7H_2O$, 0.1 g/L of $AlCl_3.6H_2O$, 0.1 g/L of $CuCl_2.H_2O$, 0.05 g/L of $H_3BO_4$, and 5M HCl. Then the cells were incubated at 35° C. and 200 rpm for 24 h.

After the fermentation, the content of 2'-fucosyllactose in the fermentation supernatant was determined by high performance liquid chromatography. The content of 2'-fucosyllactose is determined to be up to 1.042 g/L (FIG. 5).

Comparative Example 2: Production of 2'-Fucosyllactose by Fermentation with BSGL-FR The recombinant *Bacillus subtilis* BSGL-FR was prepared into a seed culture. The seed culture medium for the seed culture contained 10 g/L of peptone, 5 g/L of yeast powder, and 10 g/L of NaCl. The seed culture was prepared by picking single colonies on fresh plates into the seed culture mediums and cultured for 8-10 h.

The seed culture was inoculated into a fermentation medium in an amount to give an $OD_{600}$ value of 0.1. The fermentation medium contained 20 g/L of initial glycerol, 6 g/L of peptone, 12 g/L of yeast powder, 6 g/L $(NH_4)_2SO_4$, 12.5 g/L of $K_2HPO_4.3H_2O$, 2.5 g/L of $KH_2PO_4$, 5 g/L of $CaCO_3$, and 10 mL/L of a trace element solution comprising 1.0 g/L of $MnSO_4.5H_2O$, 0.4 g/L of $CoCl_2.6H_2O$, 0.2 g/L of $NaMoO_4.2H_2O$, 0.2 g/L of $ZnSO_4.7H_2O$, 0.1 g/L of $AlCl_3.6H_2O$, 0.1 g/L of $CuCl_2.H_2O$, 0.05 g/L of $H_3BO_4$, and 5M HCl. Then the cells were incubated at 35° C. and 200 rpm for 24 h.

After the fermentation, the content of 2'-fucosyllactose in the fermentation supernatant was determined by high performance liquid chromatography. The content of 2'-fucosyllactose is determined to be up to 1.250 g/L (FIG. 5).

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:

1. A recombinant *Bacillus subtilis* with improved 2'-fucosyllactose production, wherein the recombinant *Bacillus subtilis* is obtained by over-expressing a fusion protein of L-fucokinase/guanosine 5'-diphosphate-L-fucose pyrophosphorylase and a fucosyltransferase in *Bacillus subtilis* BSGL,
   wherein the L-fucokinase/guanosine 5'-diphosphate-L-fucose pyrophosphorylase is conjugated to the fucosyltransferase (FutC) by a linker;
   wherein the L-fucokinase/guanosine 5'-diphosphate-L-fucose pyrophosphorylase is expressed by the gene having the nucleotide sequence of GenBank: AY849806.1 on NCBI as of May 25, 2020; and the fucosyltransferase is expressed by the gene having the nucleotide sequence of GenBank: KY499613 on NCBI as of May 25, 2020; and
   wherein the linker has an amino acid sequence selected from the group consisting of SEQ ID NO:4, SEQ ID NO:5, and SEQ ID NO:6.

2. A method for constructing the recombinant *Bacillus subtilis* according to claim 1, comprising steps of:
   S1: constructing a recombinant plasmid comprising the L-fucokinase/guanosine 5'-diphosphate-L-fucose pyrophosphorylase gene, the fucosyltransferase gene and a linker gene; and
   S2: transforming the recombinant plasmid into the competent *Bacillus subtilis* BSGL cells, and confirming, by verification, the successful expression of a fusion protein of the L-fucokinase/guanosine 5'-diphosphate-L-fucose pyrophosphorylase and the fucosyltransferase, to obtain the recombinant *Bacillus subtilis*.

3. A method for producing 2'-fucosyllactose by fermentation with the recombinant *Bacillus subtilis* according to claim 1.

4. The method according to claim 3, comprising steps of:
   S1: inoculating single colonies of recombinant *E. coli* in a seed culture medium and culturing for 8-12 h to obtain a seed culture; and
   S2: inoculating the seed culture into a fermentation medium, incubating at 34-36° C. and 180-220 rpm for 20-30 h, and separating the fermentation supernatant to obtain 2'-fucosyllactose.

5. The method according to claim 4, wherein the seed culture medium comprises 8-12 g/L of tryptone, 4-6 g/L of yeast powder, and 8-12 g/L of NaCl.

6. The method according to claim 4, wherein the fermentation medium comprises 15-25 g/L of initial glycerol, 5-7 g/L of peptone, 10-15 g/L of powdery yeast, 5-7 g/L of $(NH_4)_2SO_4$, 12-13 g/L of $K_2HPO_4 \cdot 3H_2O$, 2-3 g/L of $KH_2PO_4$, 4-6 g/L of $CaCO_3$ and 8-12 mL/L of a trace element solution, and the trace element solution comprises 0.8-1.2 g/L of $MnSO_4 \cdot 5H_2O$, 0.3-0.5 g/L of $CoCl_2 \cdot 6H_2O$, 0.1-0.3 g/L of $NaMoO_4 \cdot 2H_2O$, 0.1-0.3 g/L of $ZnSO_4 \cdot 7H_2O$, 0.08-0.12 g/L of $AlCl_3 \cdot 6H_2O$, 0.08-0.12 g/L of $CuCl_2 \cdot H_2O$, 0.04-0.06 g/L of $H_3BO_4$, and 4-6M HCl.

* * * * *

SEQUENCE LISTING

<160> NUMBER OF SEQ ID NOS: 6

<210> SEQ ID NO 1
<211> LENGTH: 15
<212> TYPE: DNA
<213> ORGANISM: Artificial sequence
<220> FEATURE:
<223> OTHER INFORMATION: EK1 linker 1

<400> SEQUENCE: 1
gaagctgcgg caaaa                                                    15

<210> SEQ ID NO 2
<211> LENGTH: 30
<212> TYPE: DNA
<213> ORGANISM: Artificial sequence
<220> FEATURE:
<223> OTHER INFORMATION: EK1 linker 2

<400> SEQUENCE: 2
gaagctgcgg caaaagaagc tgcggcaaaa                                    30

<210> SEQ ID NO 3
<211> LENGTH: 45
<212> TYPE: DNA
<213> ORGANISM: Artificial sequence
<220> FEATURE:

```
<223> OTHER INFORMATION: EK1 linker 3

<400> SEQUENCE: 3
gaagctgcgg caaagaagc tgcggcaaaa gaagctgcgg caaaa         45

<210> SEQ ID NO 4
<211> LENGTH: 5
<212> TYPE: PRT
<213> ORGANISM: Artificial sequence
<220> FEATURE:
<223> OTHER INFORMATION: EK1 linker 1

<400> SEQUENCE: 4

Glu Ala Ala Ala Lys
1               5

<210> SEQ ID NO 5
<211> LENGTH: 10
<212> TYPE: PRT
<213> ORGANISM: Artificial sequence
<220> FEATURE:
<223> OTHER INFORMATION: EK1 linker 2

<400> SEQUENCE: 5

Glu Ala Ala Ala Lys Glu Ala Ala Ala Lys
1               5                   10

<210> SEQ ID NO 6
<211> LENGTH: 15
<212> TYPE: PRT
<213> ORGANISM: Artificial sequence
<220> FEATURE:
<223> OTHER INFORMATION: EK1 linker 3

<400> SEQUENCE: 6

Glu Ala Ala Ala Lys Glu Ala Ala Ala Lys Glu Ala Ala Ala Lys
1               5                   10                  15
```